(12) United States Patent
Masere et al.

(10) Patent No.: US 10,155,705 B2
(45) Date of Patent: Dec. 18, 2018

(54) STERICALLY HINDERED HYDROQUINONES AS ANTIFOULANTS FOR UNSATURATED MONOMERS

(71) Applicant: Ecolab USA Inc., St. Paul, MN (US)

(72) Inventors: Jonathan Masere, Richmond, TX (US); Ramon Colorado, Jr., Houston, TX (US)

(73) Assignee: Ecolab USA Inc., St. Paul, MN (US)

( * ) Notice: Subject to any disclaimer, the term of this patent is extended or adjusted under 35 U.S.C. 154(b) by 0 days.

(21) Appl. No.: 15/132,844

(22) Filed: Apr. 19, 2016

(65) Prior Publication Data

US 2016/0304417 A1    Oct. 20, 2016

Related U.S. Application Data

(60) Provisional application No. 62/150,022, filed on Apr. 20, 2015.

(51) Int. Cl.
    *C07C 7/20*    (2006.01)
(52) U.S. Cl.
    CPC ..................................... *C07C 7/20* (2013.01)
(58) Field of Classification Search
    CPC ............................................................ C07C 7/20
    See application file for complete search history.

(56) References Cited

U.S. PATENT DOCUMENTS

| 2,455,745 A | 12/1948 | Erickson |
| 2,783,271 A | 2/1957 | Eck et al. |
| 2,810,651 A * | 10/1957 | Thompson ............... C10M 1/08 106/263 |
| 2,965,685 A | 12/1960 | Campbell |
| 3,222,334 A | 12/1965 | Demme |
| 3,320,305 A | 5/1967 | Wiese |
| 3,696,050 A | 10/1972 | Werts et al. |
| 3,704,235 A | 11/1972 | Rassat et al. |
| 4,202,742 A | 5/1980 | Castle |
| 4,293,347 A | 10/1981 | Haschke et al. |
| 4,487,981 A | 12/1984 | Miller et al. |
| 5,221,498 A | 6/1993 | Reid et al. |
| 5,235,056 A | 8/1993 | Cunkle et al. |

(Continued)

FOREIGN PATENT DOCUMENTS

| CA | 2232502 | 9/1998 |
| CA | 2 260 310 A1 | 7/2000 |

(Continued)

OTHER PUBLICATIONS

International Search Report dated Jul. 12, 2016 related to PCT Application No. PCT/US2016/028239, 3 pages.

(Continued)

*Primary Examiner* — In Suk C Bullock
*Assistant Examiner* — Alyssa L Cepluch
(74) *Attorney, Agent, or Firm* — Stinson Leonard Street LLP

(57) ABSTRACT

The present invention generally relates to compounds and methods for preventing fouling caused by the radical polymerization of unsaturated compounds, particularly vinyl monomers. More particularly, it relates to the use of hindered hydroquinones to inhibit the polymerization, which result in the fouling of process equipment, and prematurely consume the vinylic monomer products.

11 Claims, 1 Drawing Sheet

(56) References Cited

U.S. PATENT DOCUMENTS

| | | | |
|---|---|---|---|
| 5,290,888 | A | 3/1994 | Gatechair et al. |
| 5,426,257 | A | 6/1995 | Arhancet |
| 5,489,720 | A | 2/1996 | Arhancet |
| 5,648,574 | A | 7/1997 | Arhancet |
| 5,670,692 | A | 9/1997 | Nesvadba et al. |
| 5,728,305 | A | 3/1998 | Hawkinson |
| 5,728,872 | A * | 3/1998 | Riemenschneider ... C07C 51/50 562/598 |
| 5,750,765 | A | 5/1998 | Nesvadba et al. |
| 5,773,674 | A | 6/1998 | Arhancet et al. |
| 5,932,735 | A | 8/1999 | Cunkle et al. |
| 6,180,231 | B1 | 1/2001 | Keogh |
| 6,284,936 | B2 | 9/2001 | Shahid |
| 6,342,647 | B1 | 1/2002 | Roof et al. |
| 6,500,982 | B1 | 12/2002 | Hale et al. |
| 6,525,146 | B1 | 2/2003 | Shahid |
| 6,599,326 | B1 | 7/2003 | Seltzer et al. |
| 6,686,422 | B2 | 2/2004 | Shahid |
| 6,770,222 | B1 | 8/2004 | Ukita et al. |
| 7,066,990 | B2 | 6/2006 | Wood et al. |
| 7,132,540 | B1 | 11/2006 | Jawdosiuk et al. |
| 7,282,136 | B2 | 10/2007 | Howdeshell |
| 7,309,682 | B2 | 12/2007 | Lupia et al. |
| 7,429,545 | B2 | 9/2008 | Lupia et al. |
| 7,618,644 | B2 | 11/2009 | Lupia et al. |
| 7,718,096 | B2 | 5/2010 | Yale et al. |
| 7,943,809 | B2 * | 5/2011 | Benage ............... C08F 2/40 208/48 AA |
| 8,110,650 | B2 | 2/2012 | Nava et al. |
| 8,247,593 | B2 | 8/2012 | Morrison et al. |
| 8,691,944 | B2 | 4/2014 | Clark et al. |
| 8,884,038 | B2 | 11/2014 | Masere |
| 2009/0287013 | A1 | 11/2009 | Morrison et al. |
| 2010/0168434 | A1 | 7/2010 | Loyns et al. |
| 2012/0056128 | A1 | 3/2012 | Bauchet |
| 2012/0313036 | A1 | 12/2012 | Masere |
| 2013/0178652 | A1 | 7/2013 | Fruchey et al. |
| 2014/0288337 | A1 | 9/2014 | Rinker et al. |

FOREIGN PATENT DOCUMENTS

| | | |
|---|---|---|
| CN | 102795966 A | 11/2012 |
| DE | 102008061611 A1 | 6/2009 |
| EP | 0 373 636 A1 | 6/1990 |
| EP | 0 765 856 A1 | 4/1997 |
| EP | 0 915 108 A1 | 5/1999 |
| EP | 0 943 665 A1 | 9/1999 |
| WO | 01/12677 A1 | 2/2001 |
| WO | 01/40404 A1 | 6/2001 |
| WO | 2006/078123 A1 | 7/2006 |
| WO | 2007/045886 A1 | 4/2007 |
| WO | 2008/103613 A2 | 8/2008 |
| WO | 2015/084843 A1 | 6/2015 |

OTHER PUBLICATIONS

Written Opinion dated Jul. 12, 2016 related to PCT Application No. PCT/US2016/028239, 5 pages.

Jurd, Leonard et al., New Types of Insect Chemosterilants, Benzylphenols and Benzl-1,3-benzodioxole Derivatives as Additives to Housefly Diet, Journal of Agricultural and Food Chemistry, 1979, pp. 1007-1016, vol. 27, No. 5.

King, Frank D., Bioisosteres, Conformational Restriction, and Pro-drugs—Case History: An Example of a Conformational Restriction Approach, Med. Chem., Principle and Practice (1994), pp. 206-208.

Ma, Yun, Nitroxides in Mechanistic Studies; Ageing of Gold Nanoparticles and Nitroxide Transformation in Acids, Submitted to the Department of Chemistry, University of York, 2010, 221 pages.

Miyazawa, Takeo et al., New Method for Preparation of Superoxide Ion by Use of Amino Oxide, J. Org. Chem., Dec. 1985, vol. 50, No. 25, pp. 5389-5391.

Sciannamea, Valerie et al., In-Situ Nitroxide-Mediated Radical Polymerization (NMP) Processes: Their Understanding and Optimization, Chem. Rev. 2008, vol. 108, No. 3, pp. 1104-1126.

Synthesis of Tropine & Its Derivatives, accessed from http://www.lab-q.net/synthesis/syn-tropine on Dec. 18, 2014, 6 pages.

* cited by examiner

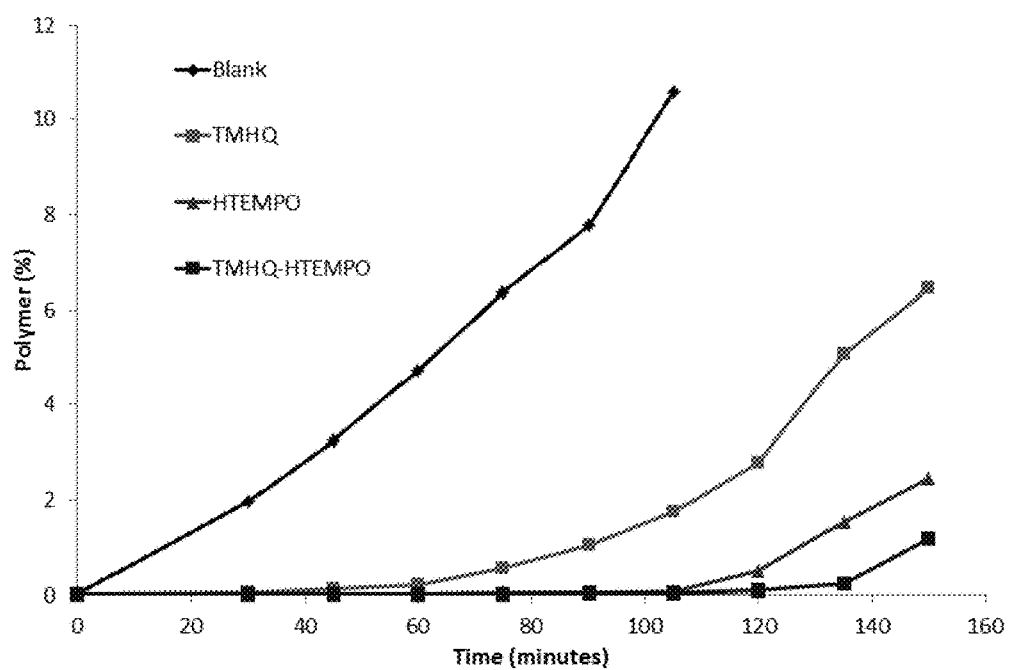

STERICALLY HINDERED HYDROQUINONES AS ANTIFOULANTS FOR UNSATURATED MONOMERS

CROSS-REFERENCE TO RELATED APPLICATION

This application claims priority to U.S. Provisional Patent Application Ser. No. 62/150,022 filed on Apr. 20, 2015, the disclosure of which is incorporated herein by reference in its entirety.

FIELD OF THE INVENTION

The present invention generally relates to compounds and methods for inhibiting the free radical polymerization of unsaturated compounds, particularly vinyl monomers. More particularly, it relates to the use of sterically hindered hydroquinone compounds to inhibit the polymerization of unsaturated compounds such as vinyl monomers that are constituents of hydrocarbon streams.

BACKGROUND OF THE INVENTION

Unsaturated compounds, particularly vinyl monomers, can undesirably polymerize at various stages of their manufacture, processing, handling, storage, and use. Vinyl monomers can undergo self-initiated polymerization at elevated temperatures even in the absence of polymerization promoters. Thus, undesired thermal polymerization can be a problem during the purification of vinylic monomers and during sudden process shutdowns. Undesirable polymerization results in product loss because the valuable monomer end product is consumed in an undesired side reaction. Moreover, unwanted polymerization results in the precipitation and deposition of polymer foulants on the process equipment thereby reducing production efficiency. Unless the unwanted polymerization is effectively controlled, this fouling of process equipment may require a shutdown of the process so as to remove the undesired polymer by physical methods. This problem is particularly acute in the manufacture and purification of vinyl aromatic monomers.

To prevent the formation of unwanted polymer as well as protecting the process equipment, the dominant products in current use are efficacious and low-cost dinitrophenols (DNP). A prototype of DNP antipolymerants in the market is 2,4-dinitro-sec-butylphenol (DNBP). It is a highly effective antipolymerant. However, DNBP is very toxic and a known environmental hazard such that is becoming highly regulated, with the ultimate objective of completely eliminating the usage of said antipolymerant. A prime example is Europe's REACH legislation. Another equally significant disadvantage is that the DNP compounds release NOx emissions during incineration. As a consequence of these disadvantages, there is a need for antipolymerant compounds that are as efficient as DNBP at reducing polymerization and yet are safe and environmentally friendly.

SUMMARY OF THE INVENTION

The present invention reveals a method for mitigating unwanted polymerization and subsequent fouling of equipment during the processing, transportation, or storage of hydrocarbon streams containing an unsaturated hydrocarbon whereby said streams are contacted with an effective amount of a hydroquinone compound of Formula 1:

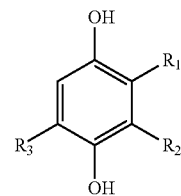

(1)

wherein $R_1$, $R_2$, and $R_3$ are independently hydrogen, alkyl, aryl, heterocyclo, or $R_1$ and $R_2$ together with the carbons they are attached to form a 5- or 6-membered fused cyclo, aryl, heterocyclo, or heteroaryl ring; wherein at least two of $R_1$, $R_2$, and $R_3$ are other than hydrogen.

Other objects and features will be in part apparent and in part pointed out hereinafter.

BRIEF DESCRIPTION OF THE DRAWINGS

FIG. 1 is a graph of the percent polymer formed versus time for various polymerization inhibitors including 2,3,5-trimethyl hydroquinone (TMHQ), 4-hydroxy-2,2,6,6-tetramethyl-1-piperidinyloxy (HTEMPO), and a combination of TMHQ and HTEMPO.

Corresponding reference characters indicate corresponding parts throughout the drawings.

DESCRIPTION OF THE PREFERRED EMBODIMENTS

The present invention is directed to methods of the use of sterically hindered hydroquinone compounds for inhibiting polymerization of unsaturated compounds like styrene, acrylic acid and its ester, methacrylic acid and esters thereof, and acrylamides, which are prone to premature polymerization of unsaturated carbon-carbon bonds. The unsaturated compound is in contact with an effective amount of a hydroquinone compound of Formula 1. The unsaturated compounds have high polymerization reactivity rates such that they readily polymerize under typical processing conditions. The undesired polymerization of the unsaturated compounds is costly due to the reduction of the desired monomer produced. Furthermore, the resultant polymer precipitates out and gets deposited on the process equipment as a foulant. The deposited foulant reduces the efficiency of the process such that shutting down the process to physically clean the fouled equipment becomes needed. Physically cleaning equipment is quite costly. Thus, methods for preventing fouling caused by this unwanted polymerization are beneficial for many hydrocarbon processes laden with vinylic species.

One aspect of the invention is a method for preventing fouling during purification, transportation, or storage of a hydrocarbon stream containing a species that have reactive unsaturated carbon-carbon bonds whereby said species is in contact with an effective amount of a hydroquinone compound of Formula 1

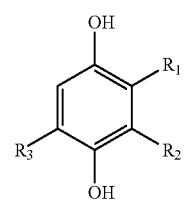

(1)

wherein $R_1$, $R_2$, and $R_3$ are independently hydrogen, alkyl, aryl, heterocyclo, or $R_1$ and $R_2$ together with the carbons they are attached to form a 5- or 6-membered fused cyclo, aryl, heterocyclo, or heteroaryl ring; wherein at least two of $R_1$, $R_2$, and $R_3$ are other than hydrogen.

For the hydroquinone compounds of Formula 1, when $R_1$ and $R_2$ together with the carbons they are attached to form a 5-membered or 6-membered fused ring, the compound has the structure of Formula 2 or Formula 3:

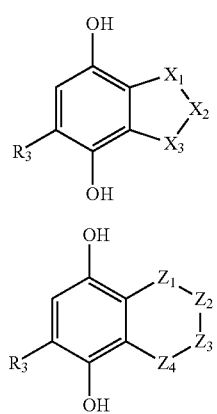

wherein $X_1$, $X_2$, and $X_3$ are independently —O—, —S—, —N($R_4$)—, or —C(H)($R_4$)—; $Z_1$, $Z_2$, $Z_3$, and $Z_4$ are independently —O—, —S—, —N($R_4$)—, or —C(H)($R_4$)—; $R_3$ is hydrogen, alkyl, aryl, or heterocyclo and; $R_4$ is independently hydrogen, alkyl, aryl, or heterocyclo.

For the compounds of Formula 2, $X_1$, $X_2$, and $X_3$ can independently be —O— or —C(H)($R_4$)—, wherein at least one of $X_1$, $X_2$, and $X_3$ is —C(H)($R_4$)—. Further, for compounds of Formula 3, $Z_1$, $Z_2$, $Z_3$, and $Z_4$ can independently be —O— or —C(H)($R_4$)— and wherein at least two of $Z_1$, $Z_2$, $Z_3$, and $Z_4$ is —C(H)($R_4$)—.

For the compounds of Formula 2, preferably, $X_1$, $X_2$, and $X_3$ can independently be —C(H)($R_4$)—, wherein $R_4$ is hydrogen. Further, for compound of Formula 3, $Z_1$, $Z_2$, $Z_3$, and $Z_4$ can independently be —C(H)($R_4$)—, wherein $R_4$ is hydrogen.

For the methods using compounds of Formula 1, $R_1$, $R_2$, and $R_3$ can be independently alkyl. Preferably, for the compounds of Formula 1, $R_1$, $R_2$, and $R_3$ can be independently methyl, ethyl, propyl, butyl, pentyl, hexyl, heptyl, or octyl. More preferably, for the compounds of Formula 1, $R_1$, $R_2$, and $R_3$ can be independently methyl, ethyl, propyl, or butyl. Most preferably, $R_1$, $R_2$, and $R_3$ can be methyl.

The methods described herein can be used for hydrocarbon streams containing ethylene, propylene, acetylene, styrene, butadiene, or a combination thereof.

Furthermore, the methods can comprise contacting the hydrocarbon stream with a nitroxide compound in combination with the hydroquinone compounds of Formula 1.

The nitroxide compounds used in combination with the hydroquinone compound of Formula 1 can be 2,2,6,6-tetramethylpiperidine-1-oxide, 4-hydroxy-2,2,6,6-tetramethylpiperidine-1-oxide, 4-methoxy-2,2,6,6-tetramethylpiperidine-1-oxide, 4-ethoxy-2,2,6,6-tetramethylpiperidine-1-oxide, 4-propoxy-2,2,6,6-tetramethylpiperidine-1-oxide, 4-butoxy-2,2,6,6-tetramethylpiperidine-1-oxide, or a combination thereof. Preferably, the nitroxide compound can be 2,2,6,6-tetramethylpiperidine-1-oxide, 4-hydroxy-2,2,6,6-tetramethylpiperidine-1-oxide, 4-butoxy-2,2,6,6-tetramethylpiperidine-1-oxide, or a combination thereof. More preferably, the nitroxide compound comprises 4-hydroxy-2,2,6,6-tetramethylpiperidine-1-oxide.

The polymerization inhibition method can also prevent unwanted polymerization and the fouling of the process equipment in a primary fractionation process, light ends fractionation, non-aromatic halogenated vinyl fractionation, process-gas compression, dilution steam system, caustic tower, quench water tower, butadiene extraction, propane dehydrogenation, diesel and petrol fuel stabilization, olefin metathesis, styrene purification, hydroxyhydrocarbon purification, or delays the polymerization of resins and compositions comprising ethylenically unsaturated species. Preferably, the polymerization inhibition method can prevent fouling due to the polymerization of the unsaturated and reactive compounds in the butadiene extraction or styrene purification processes.

Another aspect of the invention is a composition comprising a compound of Formula 1 and a solvent. Suitable organic solvents include, and are not limited to, pentane, heptane, hexane, benzene, ethylbenzene, toluene, or a combination thereof.

The composition can comprise one or more additional polymerization inhibitors. Compounds that are suitable as additional polymerization inhibitors in the inventive composition include phenols, alkylated phenols, nitrophenols, nitrosophenols, quinones, hydroquinones, quinone ethers, quinone methides, amines, hydroxylamines, and phenothiazines.

Further, the composition comprising the compound of Formula 1 and a solvent can further comprise a nitroxide compound. This nitroxide compound can be 2,2,6,6-tetramethylpiperidine-1-oxide, 4-hydroxy-2,2,6,6-tetramethylpiperidine-1-oxide, 4-methoxy-2,2,6,6-tetramethylpiperidine-1-oxide, 4-ethoxy-2,2,6,6-tetramethylpiperidine-1-oxide, 4-propoxy-2,2,6,6-tetramethylpiperidine-1-oxide, 4-butoxy-2,2,6,6-tetramethylpiperidine-1-oxide, or a combination thereof. Preferably, the nitroxide compound can be 2,2,6,6-tetramethylpiperidine-1-oxide, 4-hydroxy-2,2,6,6-tetramethylpiperidine-1-oxide, 4-butoxy-2,2,6,6-tetramethylpiperidine-1-oxide, or a combination thereof. More preferably, the nitroxide compound comprises 4-hydroxy-2,2,6,6-tetramethylpiperidine-1-oxide.

The polymerization inhibitor compositions described herein can be introduced into the monomer to be protected by any conventional method. It can be added as a concentrate solution in suitable solvents just upstream of the point of desired application by suitable means. In addition, these compounds can be injected separately into the distillation train with the incoming feed, or through separate entry points providing efficient distribution of the inhibitor composition. Since the inhibitor is gradually depleted during operation, it is generally necessary to maintain the appropriate amount of the inhibitor in the distillation apparatus by adding inhibitor during the course of the distillation process. This addition may be carried out either on a generally continuous basis or by intermittently charging inhibitor into the distillation system if the concentration of inhibitor is to be maintained above the minimum required level.

The effective amount of a compound of Formulae 1, 2, and 3 can be from about 0.1 mmolal to 5 mmolal, from about 0.1 mmolal to 4 mmolal, from about 0.1 mmolal to 3 mmolal, from about 0.1 mmolal to 2 mmolal, from about 0.2 mmolal to 5 mmolal, from about 0.2 mmolal to 4 mmolal, from about 0.2 mmolal to 3 mmolal; preferably, from about 0.2 mmolal to about 2 mmolal.

Unless otherwise indicated, an alkyl group as described herein alone or as part of another group is an optionally substituted linear saturated monovalent hydrocarbon substituent containing from one to sixty carbon atoms and preferably one to thirty carbon atoms in the main chain or eight to thirty carbon atoms in the main chain, or an optionally substituted branched saturated monovalent hydrocarbon substituent containing three to sixty carbon atoms, and preferably eight to thirty carbon atoms in the main chain. Examples of unsubstituted alkyl groups include methyl, ethyl, n-propyl, i-propyl, n-butyl, i-butyl, s-butyl, t-butyl, n-pentyl, i-pentyl, s-pentyl, t-pentyl, and the like.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl, bicyclo[2.2.2]octanyl and the like. Representative cycloalkyl groups include cyclopropyl, cyclobutyl, cyclopentyl, cyclohexyl, bicyclo[2.2.1]heptanyl, bicyclo[2.2.2]octanyl, and the like.

The term "heteroaryl," as used herein, refers to a monocyclic, bicyclic, or tricyclic aromatic heterocyclic group containing one or more heteroatoms (e.g., 1 to 3 heteroatoms) selected from O, S and N in the ring(s). Heteroaryl groups include, but are not limited to, pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, and indolyl. Heteroaryl groups can be unsubstituted or substituted by one or more suitable substituents, preferably 1 to 5 suitable substituents, as defined above.

The term "heterocyclo," "heterocycle," or "heterocyclyl," as used herein, refers to a monocyclic, bicyclic, or tricyclic group containing 1 to 4 heteroatoms selected from N, O, $S(O)_n$, $P(O)_n$, $PR^z$, NH or $NR^z$, wherein $R^z$ is a suitable substituent. Heterocyclic groups optionally contain one or two double bonds. Heterocyclic groups include, but are not limited to, azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydro-thiadiazinyl, morpholinyl, oxetanyl, tetrahydrodiazinyl, oxazinyl, oxathiazinyl, indolinyl, isoindolinyl, quinuclidinyl, chromanyl, isochromanyl, and benzoxazinyl. Examples of monocyclic saturated or partially saturated ring systems are tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholin-yl, 1,2-tetrahydrothiazin-2-yl, 1,3-tetrahydrothiazin-3-yl, tetrahydrothiadiazin-yl, morpholin-yl, 1,2-tetrahydrodiazin-2-yl, 1,3-tetrahydrodiazin-1-yl, 1,4-oxazin-2-yl, and 1,2,5-oxathiazin-4-yl. Heterocyclic groups can be unsubstituted or substituted by one or more suitable substituents, preferably 1 to 3 suitable substituents, as defined above.

The terms "aryl" or "ar" as used herein alone or as part of another group (e.g., aralkyl or alkaryl) denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl. The term "aryl" also includes heteroaryl.

The term "substituted" as in "substituted aryl," "substituted alkyl," and the like, means that in the group in question (i.e., the alkyl, aryl or other group that follows the term), at least one hydrogen atom bound to a carbon atom is replaced with one or more substituent groups such as hydroxy (—OH), alkylthio, phosphino, amido (—CON($R_A$)($R_B$), wherein $R_A$ and $R_B$ are independently hydrogen, alkyl, or aryl), amino(—N($R_A$)($R_B$), wherein $R_A$ and $R_B$ are independently hydrogen, alkyl, or aryl), halo (fluoro, chloro, bromo, or iodo), silyl, nitro (—$NO_2$), an ether (—$OR_A$ wherein $R_A$ is alkyl or aryl), an ester (—OC(O)$R_A$ wherein $R_A$ is alkyl or aryl), keto (—C(O)$R_A$ wherein $R_A$ is alkyl or aryl), heterocyclo, and the like. When the term "substituted" introduces a list of possible substituted groups, it is intended that the term apply to every member of that group. That is, the phrase "optionally substituted alkyl or aryl" is to be interpreted as "optionally substituted alkyl or optionally substituted aryl."

"Alkaryl" means an aryl group attached to the parent molecule through an alkylene group. The number of carbon atoms in the aryl group and the alkylene group is selected such that there is a total of about 6 to about 18 carbon atoms in the alkaryl group. A preferred alkaryl group is benzyl.

"Vinyl monomer" refers to a monomer comprising at least one carbon-carbon double bond. The monomer can be substituted with various groups, such as acids (e.g., acrylic acid), esters (e.g., acrylate esters), halogen (e.g., vinyl chloride), aryl (e.g., styrene, vinyl toluene, divinylbenzene), cyano (e.g., acrylonitrile), and acetoxy (e.g., vinyl acetate). The monomer can be conjugated (e.g., butadiene, cyclopentadiene, vinyl acetylene, indene, and the like).

A polymerization "inhibitor" refers to a composition of matter that is able to scavenge radicals in a radical polymerization process. Inhibitors can be used to stabilize monomers and prevent their polymerization or quench polymerization when a desired conversion is achieved. They can also be used to regulate or control the kinetics of a polymerization process.

"Refining" of a hydrocarbon stream means to separate and/or purify constituent components.

Having described the invention in detail, it will be apparent that modifications and variations are possible without departing from the scope of the invention defined in the appended claims.

EXAMPLES

The foregoing may be better understood by reference to the following examples, which are presented for purposes of illustration and are not intended to limit the scope of the invention.

Example 1: Performance of TMHQ

The antipolymerant performance of TMHQ was determined using the static method in which a 0.31 mM solution of the antipolymerant was prepared in inhibitor-free styrene. The stabilizer in the commercial styrene, 4-tert-butylcatechol (TBC), was removed using an alumina column. A solution comprising 0.31 mM of TMHQ was prepared by dissolving 0.0179 g the in freshly de-inhibited styrene 350 g of solution. Each of twenty-four Ace Glass #15 threaded pressure tubes equipped with PTFE screw caps and fluoroelastomer (FETFE) O-rings were charged with 9 mL of the solution. Dissolved oxygen was purged out of the solutions by sparging with nitrogen for 2 minutes. Once sparged, each tube was immediately sealed and the solution kept under a nitrogen headspace. The tubes were loaded into a heating block that had been preheated to 120° C. After 30 minutes, and every 15 minutes thereafter, four tubes were retrieved from the block and the polymerization reaction quenched by cooling in an ice bath. The cooled polymer solutions were immediately diluted with toluene.

To measure the amount of polymer formed, methanol was used to precipitate the polymer in accordance with the ASTM D2121 method. The absorbance of the polymer-methanol solutions were measured at 420 nm. Using a calibration curve, the polymer concentrations in each of the tubes was measured and the four data points for each time were averaged.

A proprietary method was also used to measure the polymer in the diluted analyte solutions.

Example 2: TMHQ plus 4-hydroxy-2,2,6,6-tetra-methylpiperidinoxy (HTEMPO)

TMHQ (0.0090 g) and HTEMPO (0.0100 g) were dissolved in de-inhibited styrene to give a 0.16 mM TMHQ and a 0.16 mM HTEMPO solution. Using the procedure in Example 1, the antipolymerant activity of the combination of TMHQ and HTEMPO was determined.

Example 3: 4-hydroxy-2,2,6,6-tetra-methylpiperidinoxy (HTEMPO)

HTEMPO (0.0199 g) was dissolved in de-inhibited styrene to give a 0.33 mM solution. Using the procedure in Example 1, the antipolymerant activity of HTEMPO was determined.

Example 4: Untreated Styrene

Immediately after removing TBC from styrene, 9 g aliquots of the styrene were charged into each of the aforementioned pressure tubes. After the dissolved oxygen was purged out of the solutions, polymerization reactions, and polymer analysis were conducted in accordance with the procedure in Example 1.

| Time (minutes) | (w/w) Polymer (polystyrene) Concentration Percentage | | | |
|---|---|---|---|---|
| | Blank | TMHQ | HTEMPO | TMHQ-HTEMPO |
| 0 | 0 | 0 | 0 | 0 |
| 30 | 1.96 | 0.044 | 0.0135 | 0.0133 |
| 45 | 3.24 | 0.110 | 0.0187 | 0.0158 |
| 60 | 4.72 | 0.214 | 0.0237 | 0.0229 |
| 75 | 6.36 | 0.543 | 0.0263 | 0.0232 |
| 90 | 7.78 | 1.04 | 0.0366 | 0.0298 |
| 105 | 10.57 | 1.75 | 0.0693 | 0.0510 |
| 120 | | 2.79 | 0.492 | 0.0850 |
| 135 | | 5.06 | 1.53 | 0.237 |
| 150 | | 6.45 | 2.47 | 1.18 |

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compounds and methods without departing from the scope of the invention, it is intended that all matter contained in the above description shall be interpreted as illustrative and not in a limiting sense.

What is claimed is:

1. A method for inhibiting polymerization during refining, transport, or storage of a hydrocarbon stream containing a hydrocarbon having an unsaturated carbon-carbon bond comprising contacting the hydrocarbon product with an effective amount of a hydroquinone compound has the structure of formula (2) or formula (3):

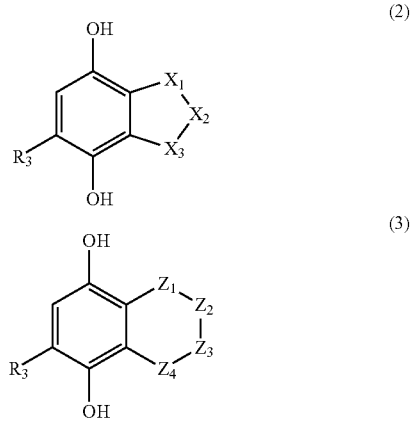

wherein
$X_1$, $X_2$, and $X_3$ are independently —O— or —C(H)($R_4$)— and wherein at least one of $X_1$, $X_2$, and $X_3$ is —C(H)($R_4$)—;
$Z_1$, $Z_2$, $Z_3$, and $Z_4$ are independently —O— or —C(H)($R_4$)— and wherein at least two of $Z_1$, $Z_2$, $Z_3$, and $Z_4$ is —C(H)($R_4$)—;
$R_3$ is hydrogen, alkyl, aryl, or heterocyclo;
$R_4$ is independently hydrogen, alkyl, aryl, or heterocyclo; and
wherein the hydroquinone compound inhibits polymerization of the hydrocarbon having an unsaturated carbon-carbon bond, and the hydrocarbon having an unsaturated carbon-carbon bond comprises ethylene, propylene, acetylene, styrene, butadiene, or a combination thereof.

2. The method of claim 1, wherein the compound has the structure of formula (2).

3. The method of claim 1, wherein the compound has the structure of formula (3).

4. The method of claim 1, wherein the hydrocarbon having an unsaturated carbon-carbon bond comprises ethylene, propylene, acetylene, butadiene, or a combination thereof.

5. The method of claim 1, wherein the method stabilizes and inhibits polymerization of the hydrocarbon having an unsaturated carbon-carbon bond during a purification or a storage process.

6. The method of claim 5, wherein the method stabilizes and inhibits polymerization of a hydrocarbon having an unsaturated carbon-carbon bond in a primary fractionation process, process-gas compression, butadiene extraction, propane dehydrogenation, diesel and petrol fuel stabilization, olefin metathesis, styrene purification, hydroxyhydrocarbon purification, or delays the polymerization of resins and compositions comprising ethylenically unsaturated species.

7. The method of claim 6, wherein the process is butadiene extraction or styrene purification.

8. The method of claim 1, further comprising contacting the hydrocarbon stream with a nitroxide compound in combination with the hydroquinone of Formula 1.

9. The method of claim 8, wherein the nitroxide compound is 2,2,6,6-tetramethylpiperidine-1-oxide, 4-hydroxy-2,2,6,6-tetramethylpiperidine-1-oxide, 4-methoxy-2,2,6,6-tetramethylpiperidine-1-oxide, 4-ethoxy-2,2,6,6-tetramethylpiperidine-1-oxide, 4-propoxy-2,2,6,6-tetramethylpiperidine-1-oxide, 4-butoxy-2,2,6,6-tetramethylpiperidine-1-oxide, or a combination thereof.

10. The method of claim 8, wherein the nitroxide compound is 2,2,6,6-tetramethylpiperidine-1-oxide, 4-hydroxy-2,2,6,6-tetramethylpiperidine-1-oxide, 4-butoxy-2,2,6,6-tetramethylpiperidine-1-oxide, or a combination thereof.

11. The method of claim 8, wherein the nitroxide compound comprises 4-hydroxy-2,2,6,6-tetramethylpiperidine-1-oxide.

* * * * *